US00PP20928P2

(12) United States Plant Patent
Michalik

(10) Patent No.: US PP20,928 P2
(45) Date of Patent: Apr. 13, 2010

(54) *GERANIUM* PLANT NAMED 'PACVIMP'

(50) Latin Name: *Pelargonium×hortorum*
Varietal Denomination: Pacvimp

(75) Inventor: Andrea Michalik, Dresden (DE)

(73) Assignee: Elsner PAC Jungpflanzen GbR, Dresden (DE)

( * ) Notice: Subject to any disclaimer, the term of this patent is extended or adjusted under 35 U.S.C. 154(b) by 0 days.

(21) Appl. No.: 12/291,549

(22) Filed: Nov. 12, 2008

(51) Int. Cl.
*A01H 5/00* (2006.01)

(52) U.S. Cl. ..... Plt./330

(58) Field of Classification Search ..... Plt./330
See application file for complete search history.

*Primary Examiner*—Susan B McCormick Ewoldt
(74) *Attorney, Agent, or Firm*—C. A. Whealy

(57) ABSTRACT

A new and distinct cultivar of Zonal *Geranium* plant named 'Pacvimp', characterized by its compact, upright and rounded plant habit; freely branching habit; moderately vigorous growth habit; dark green-colored leaves; freely flowering habit; semi-double bright dark red-colored flowers; and good garden performance.

1 Drawing Sheet

Botanical designation: *Pelargonium×hortorum*.
Cultivar denomination: 'Pacvimp'.

BACKGROUND OF THE INVENTION

The present invention relates to a new and distinct cultivar of Zonal *Geranium* plant, botanically known as *Pelargonium×hortorum*, and hereinafter referred to by the name 'Pacvimp'.

The new Zonal *Geranium* plant is a product of a planned breeding program conducted by the Inventor in Dresden, Germany. The objective of the breeding program is to create new compact semi-double flowered Zonal *Geranium* cultivars with uniform plant habit, dark green-colored foliage and attractive flower coloration.

The new Zonal *Geranium* plant originated from a cross-pollination made by the Inventor in Dresden, Germany during the summer of 2003 of two unnamed proprietary selections of *Pelargonium×hortorum*, not patented. The new Zonal *Geranium* was discovered and selected by the Inventor as a single flowering plant from within the progeny of the stated cross-pollination in a controlled greenhouse environment in Dresden, Germany in June, 2004.

Asexual reproduction of the new Zonal *Geranium* plant by vegetative terminal cuttings in a controlled greenhouse environment in Dresden, Germany since December, 2004, has shown that the unique features of this new Zonal *Geranium* are stable and reproduced true to type in successive generations.

SUMMARY OF THE INVENTION

Plants of the new Zonal *Geranium* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Pacvimp'. These characteristics in combination distinguish 'Pacvimp' as a new and distinct cultivar of Zonal *Geranium:*

1. Compact, upright and rounded plant habit.
2. Freely branching habit.
3. Moderately vigorous growth habit.

4. Dark green-colored leaves.
5. Freely flowering habit.
6. Semi-double bright dark red-colored flowers.
7. Good garden performance.

Plants of the new Zonal *Geranium* differ primarily from plants of the parent selections in plant vigor and flower color.

Plants of the new Zonal *Geranium* can be compared to plants of *Pelargonium×hortorum* 'Pacvi', disclosed in U.S. Plant Pat. No. 14,209. In side-by-side comparisons conducted in Dresden, Germany, plants of the new Zonal *Geranium* differed from plants of 'Pacvi' in the following characteristics:

1. Plants of the new Zonal *Geranium* were more compact and rounded than plants of 'Pacvi'.
2. Plants of the new Zonal *Geranium* were more freely branching than plants of 'Pacvi'.
3. Leaves of plants of the new Zonal *Geranium* had a more distinct zonation pattern than plants of 'Pacvi'.
4. Plants of the new Zonal *Geranium* had more flowers per umbel than plants of 'Pacvi'.
5. Plants of the new Zonal *Geranium* had shorter pedicels than plants of 'Pacvi'.

BRIEF DESCRIPTION OF THE PHOTOGRAPH

The accompanying colored photograph illustrates the overall appearance of the new Zonal *Geranium* plant, showing the colors as true as it is reasonably possible to obtain in colored reproductions of this type. Colors in the photograph may differ slightly from the color values cited in the detailed botanical description which accurately describe the colors of the new Zonal *Geranium.*

The photograph comprises a side perspective view of a typical flowering plant of 'Pacvimp' grown in a container.

DETAILED BOTANICAL DESCRIPTION

The aforementioned photograph and following observations, measurements and values describe plants grown in Dresden, Germany in a glass-covered greenhouse during the autumn and winter and under conditions which closely approximate commercial *Geranium* production. During the production of the plants, day temperatures averaged 18° C., night temperatures averaged 16° C. and light levels ranged from 15 kilolux to 100 kilolux. Plants were four months from planting when the photograph and description were taken. In the detailed description, color references are made to The Royal Horticultural Society Colour Chart, 1995 Edition, except where general terms of ordinary dictionary significance are used.

Botanical classification: *Pelargonium×hortorum* 'Pacvimp'.

Parentage:

*Female, or seed, parent*.—Unnamed proprietary selection of *Pelargonium×hortorum*, not patented.

*Male or pollen parent*.—Unnamed proprietary selection of *Pelargonium×hortorum*, not patented.

Propagation:

*Type*.—By vegetative terminal cuttings.

*Time to initiate roots, summer*.—About 18 days at temperatures of 20° C.

*Time to initiate roots, winter*.—About 22 days at temperatures of 20° C.

*Time to produce a rooted young plant, summer*.—About 25 days at temperatures of 20° C.

*Time to produce a rooted young plant, winter*.—About 30 days at temperatures of 20° C.

*Root description*.—Fine, fibrous; white in color.

*Rooting habit*.—Freely branching; dense.

Plant description:

*Plant/growth habit*.—Compact, upright to rounded plant habit; densely foliated; moderately vigorous growth habit. Freely basal branching habit with about seven lateral branches developing per plant.

*Plant height, to top of umbels*.—About 25 cm.

*Plant height, to top of leaves*.—About 15 cm.

*Plant width*.—About 30 cm.

*Lateral branches*.—Length: About 10 cm. Diameter: About 8 mm. Internode length: About 1 cm. Texture: Pubescent. Color: Close to 144A.

Foliage description:

*Arrangement*.—Alternate or opposite; simple.

*Length*.—About 4 cm.

*Width*.—About 7 cm.

*Shape*.—Reniform.

*Apex*.—Rounded.

*Base*.—Cordate.

*Margin*.—Crenate.

*Venation pattern*.—Palmate.

*Texture, upper and lower surfaces*.—Pubescent; velvety.

*Color*.—Developing and fully expanded leaves, upper surface: Close to 137A; venation, close to 137A. Developing and fully expanded leaves, lower surface: Close to 146B; venation, close to 146C. Zonation pattern: Intensity: Medium to weak. Width: About 2 cm. Color: Close to 137A. Petiole: Length: About 5 cm. Diameter: About 2 mm. Texture, upper and lower surfaces: Pubescent; rough. Color, upper and lower surfaces: Close to 146B.

Flower description:

*Flower arrangement*.—Semi-double rotate flowers arranged in rounded hemispherical umbels arising from apical leaf axils. Umbels displayed above the foliage on strong peduncles. Flowers face upright to outward; flowers flat to slightly cupped. Flowers not fragrant.

*Quantity of flowers*.—Freely flowering habit; about ten flower umbels per plant each with about 18 flower buds and open flowers.

*Time to flower*.—Early flowering habit, plants begin to flower about 90 days after planting.

*Flowering season*.—Year-round under greenhouse conditions. In the garden in Dresden, Germany, flowering is continuous from April until frost in the autumn.

*Flower longevity*.—Individual flowers last about six to ten days on the plant; umbels last about three to four weeks on the plant; flowers persistent.

*Umbel height*.—About 5 cm.

*Umbel diameter*.—About 8 cm.

*Flower diameter*.—About 4 cm.

*Flower depth* (*height*).—About 1.5 cm.

*Flower buds*.—Length: About 8 mm. Diameter: About 5 mm. Shape: Rounded. Color: Close to 144A.

*Petals*.—Quantity per flower: About eight; imbricate. Length: About 2.2 cm. Width: About 2.2 cm. Shape: Obovate. Apex: Rounded. Base: Attenuate. Margin: Entire. Texture, upper and lower surfaces: Smooth, glabrous; velvety. Color: When opening and fully opened, upper surface: Close to 45B; at the base, close to 155D; venation, close to 45B. Color does not fade with development. When opening and fully opened, lower surface: Close to 40A; at the base, close to 155D; venation, close to 40A.

*Petaloids*.—None observed.

*Sepals*.—Quantity per flower: Five, arranged in a single whorl. Length: About 1 cm. Width: About 3 mm. Shape: Lanceolate. Apex: Acute. Margin: Entire. Texture, upper and lower surfaces: Pubescent. Color, upper and lower surfaces: Close to 144A.

*Peduncle* (*umbel stem*).—Length: About 10 cm to 13 cm. Diameter: About 3 mm. Strength: Strong. Angle: Mostly erect. Texture: Pubescent. Color: Close to 144A.

*Pedicel* (*individual flower stem*).—Length: About 2.5 cm. Diameter: About 1.5 mm. Strength: Moderately strong; flexible. Texture: Pubescent. Color: Close to 144A.

*Reproductive organs*.—Androecium: Stamen quantity per flower: About eight. Anther length: About 2 mm. Anther shape: Tubular. Anther color: Close to 176A. Pollen amount: Abundant. Pollen color: Close to 25A. Gynoecium: Pistil quantity per flower: One. Pistil length: About 8 mm. Stigma shape: Five-parted. Stigma color: Close to 45A. Style length: About 3 mm. Style color: Close to 45A. Ovary color: Close to 141D.

*Seeds*.—Shape: Elliptic. Length: About 3 mm. Diameter: About 1 mm. Color: Close to 165A.

Disease/pest resistance: Plants of the new Zonal *Geranium* have not been observed to be resistant to pathogens and pests common to Zonal *Geraniums*.

Garden performance: Plants of the new Zonal *Geranium* have been observed to tolerate rain, wind and temperatures ranging from about 0° C. to about 35° C. to 40° C. and have demonstrated good garden performance.

It is claimed:

1. A new and distinct Zonal *Geranium* plant named 'Pacvimp' as illustrated and described.

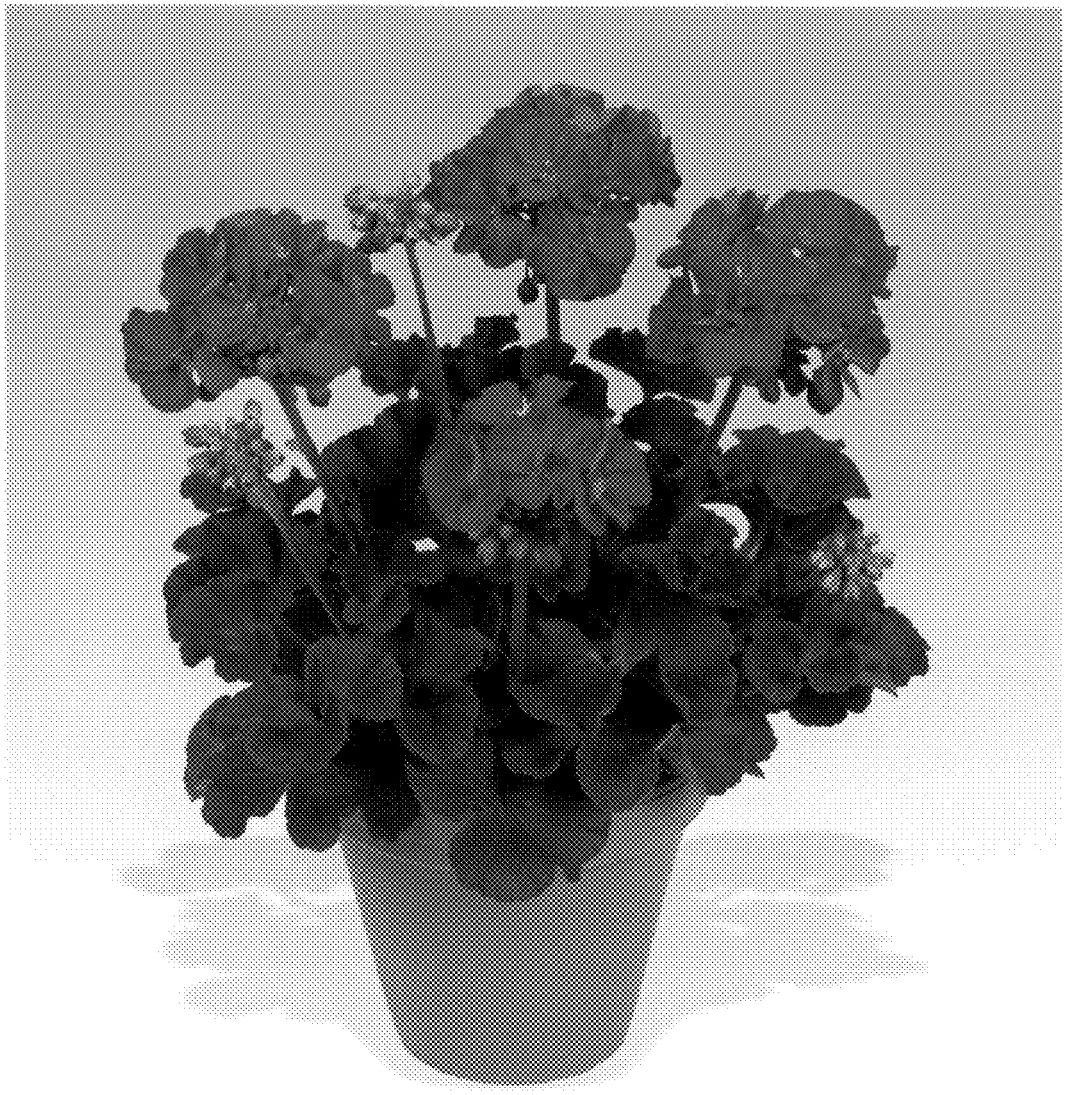

* * * * *